US008258678B2

(12) United States Patent
Buccafusca et al.

(10) Patent No.: US 8,258,678 B2
(45) Date of Patent: Sep. 4, 2012

(54) SHORT RANGE ULTRASONIC DEVICE WITH BROADBEAM ULTRASONIC TRANSDUCERS

(75) Inventors: Osvaldo Buccafusca, Fort Collins, CO (US); Steven Martin, Fort Collins, CO (US); Bruce Beaudry, Windsor, CO (US)

(73) Assignee: Avago Technologies Wireless IP (Singapore) Pte. Ltd., Singapore (SG)

( * ) Notice: Subject to any disclaimer, the term of this patent is extended or adjusted under 35 U.S.C. 154(b) by 250 days.

(21) Appl. No.: 12/710,724

(22) Filed: Feb. 23, 2010

(65) Prior Publication Data

US 2011/0204749 A1    Aug. 25, 2011

(51) Int. Cl.
 *H01L 41/08* (2006.01)
(52) U.S. Cl. ............... 310/334; 310/336; 310/337
(58) Field of Classification Search ........... 310/334–337
 See application file for complete search history.

(56) References Cited

U.S. PATENT DOCUMENTS

| 2,875,355 | A | | 2/1959 | Petermann |
| 2,943,278 | A | | 6/1960 | Mattiat |
| 2,949,772 | A | * | 8/1960 | Kritz ..................... 73/861.27 |
| 2,976,501 | A | | 3/1961 | Mattiat |
| 3,384,767 | A | | 5/1968 | Arnold et al. |
| 4,129,799 | A | | 12/1978 | Green |
| 4,529,904 | A | | 7/1985 | Hattersley |
| 4,868,446 | A | | 9/1989 | Kumada |
| 4,985,296 | A | | 1/1991 | Mortimer, Jr. |
| 5,214,343 | A | * | 5/1993 | Baumoel .................. 310/334 |
| 5,663,505 | A | | 9/1997 | Nakamura |
| 5,784,340 | A | | 7/1998 | Kanai |
| 5,814,922 | A | | 9/1998 | Uchino et al. |
| 6,040,654 | A | | 3/2000 | Le Letty |
| 6,346,764 | B1 | | 2/2002 | Boyd |
| 6,362,559 | B1 | | 3/2002 | Boyd |
| 6,667,566 | B2 | | 12/2003 | Kim et al. |
| 6,912,918 | B1 | * | 7/2005 | Lynnworth et al. ........ 73/861.26 |
| 6,919,669 | B2 | | 7/2005 | Bryant et al. |
| 7,224,105 | B2 | | 5/2007 | Onishi et al. |
| 7,389,569 | B2 | * | 6/2008 | Shiraishi et al. ............ 29/25.35 |
| 7,538,477 | B2 | | 5/2009 | Fazzio et al. |
| 7,579,753 | B2 | | 8/2009 | Fazzio et al. |
| 2002/0030424 | A1 | | 3/2002 | Iwata |
| 2005/0194867 | A1 | | 9/2005 | Kawakubo et al. |
| 2008/0122317 | A1 | | 5/2008 | Fazzio et al. |
| 2008/0122320 | A1 | | 5/2008 | Fazzio et al. |
| 2010/0164433 | A1 | * | 7/2010 | Janefalkar et al. ........... 320/115 |

(Continued)

FOREIGN PATENT DOCUMENTS

CA             2268415         10/2000

(Continued)

OTHER PUBLICATIONS

Hazas, et al. "A High Performance Privacy-Oriented Location System", Proceedings of the First IEEE International Conference on Pervasive Computing and Communications (PerCom'03).
"Overview for Applying Ultrasonic Technology", Ultrasonic Transducers, Airmar Technology Corporation, www.airmar.com.
Reid, et al. "Piezoelectric Microphone with On-Chip CMOS Circuits", Journal of Microelectromechanical Systems, Sep. 1993, p. 111-120, vol. 2, No. 3.

(Continued)

*Primary Examiner* — Mark Budd (57) ABSTRACT

An apparatus comprises a first transducer support configured to receive a first transducer in a first opening. A face of the first face of the transducer is located in a first plane. The apparatus also comprises a second transducer support configured to receive a second transducer in a second opening. A face of the second transducer is located in a second plane substantially parallel to the first plane.

19 Claims, 6 Drawing Sheets

U.S. PATENT DOCUMENTS

2010/0327702 A1 * 12/2010 Martin et al. ................ 310/346

FOREIGN PATENT DOCUMENTS

| | | |
|---|---|---|
| CN | 201110773 | 9/2008 |
| EP | 451533 | 10/1991 |
| EP | 1260834 | 11/2005 |
| JP | 4959526 | 8/1972 |
| JP | 59019384 | 1/1984 |
| JP | 59146298 | 8/1984 |
| JP | 5232241 | 9/1993 |

OTHER PUBLICATIONS

Niu, et al. "Piezoelectric Bimorph Microphone Built on Micromachined Parylene Diaphragm", Journal of Microelectromechanical Systems, Dec. 2003, p. 892-898, vol. 12, No. 6.

Loeppert, et al. "SiSonic—The First Commercialized MEMS Microphone", Solid State Sensors, Actuators, and Microsystems Workshop, p. 27-30, Hilton Head Island, South Carolina, Jun. 4-8, 2006.

* cited by examiner

FIG. 4C though the claims may reflect singular reference.

SHORT RANGE ULTRASONIC DEVICE WITH BROADBEAM ULTRASONIC TRANSDUCERS

CROSS-REFERENCE TO RELATED APPLICATIONS

The present application is related to commonly owned U.S. Pat. No. 7,579,753, to R. Shane Fazzio, et al. entitled TRANSDUCERS WITH ANNULAR CONTACTS and filed on Nov. 27, 2006; and U.S. Pat. No. 7,538,477 to R. Shane Fazzio, et al. entitled MULTI-LAYER TRANSDUCERS WITH ANNULAR CONTACTS and filed on Apr. 19, 2007. The entire disclosures of the cross-referenced patents are specifically incorporated herein by reference.

BACKGROUND

Ultrasonic transducers emit ultrasonic acoustic waves when an electrical signal is applied to thereto and/or produce an electronic signal when an ultrasonic signal is incident thereon.

One type of ultrasonic transducer is known as a piezoelectric ultrasonic transducer. A piezoelectric ultrasonic transducer comprises a piezoelectric material disposed between electrodes. The application of a time-varying electrical signal will cause a mechanical vibration across the transducer, resulting in emission of an acoustic signal. By contrast, the application of a time-varying acoustic signal to the piezoelectric ultrasonic transducer will cause a time-varying electrical signal to be generated by the piezoelectric material of the transducer. Many known ultrasonic transducers have a narrow transmission beam and a narrow acceptance angle.

Ultrasonic transducers may be used in a variety of applications. For example, ultrasonic transducers may be used in measurement and error detection applications. One type of measurement applications is based on the degree of absorption of ultrasonic waves between an ultrasonic transmitter and an ultrasonic receiver.

Figure 1:
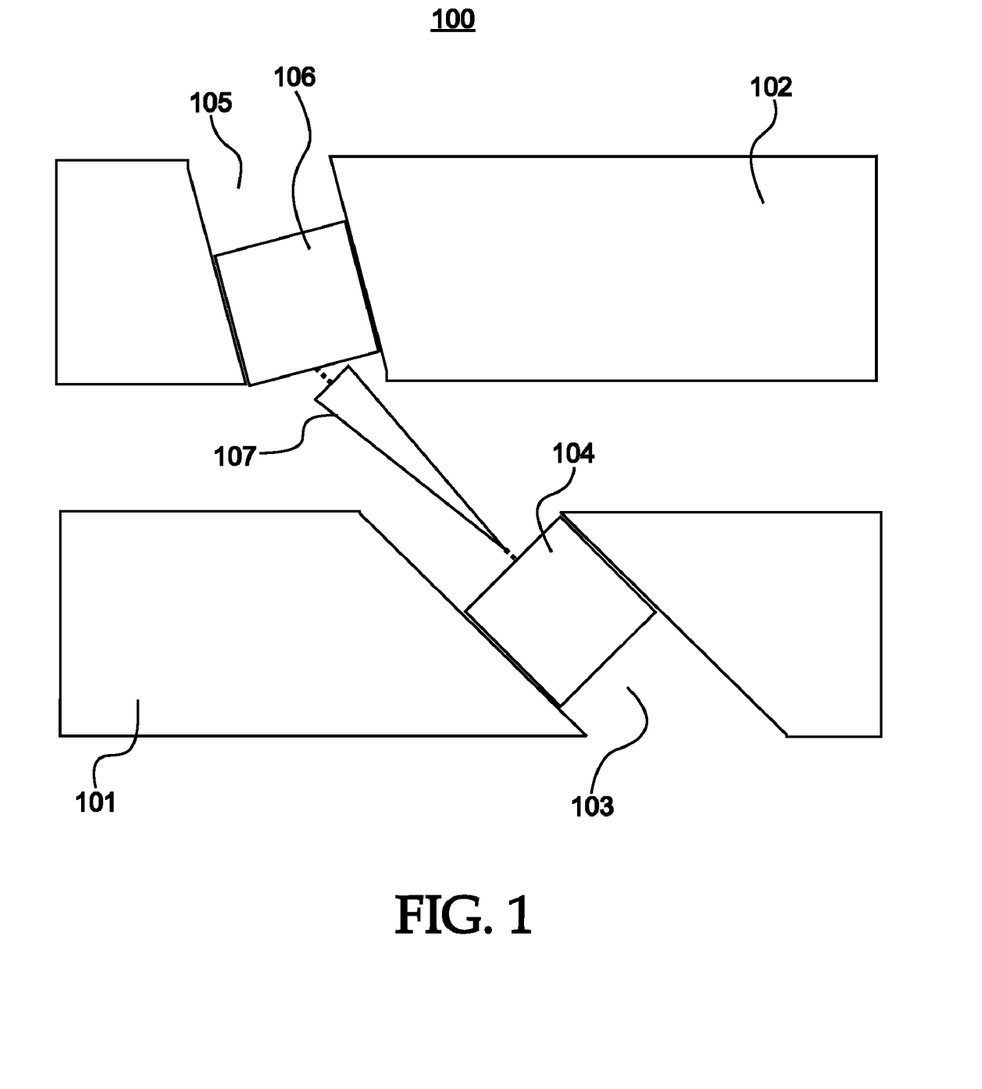
FIG. 1 depicts a known ultrasonic apparatus.

One known arrangement comprising ultrasonic transducers for absorption measurement utilizes common narrow beam transducers and is shown in FIG. 1. An ultrasonic apparatus 100 includes a transmitter support 101 and a receiver support 102. The transmitter support 101 includes a first receptacle 103, in which a transmit ultrasonic transducer 104 is provided. The receiver support 102 includes a second receptacle 105, in which a receive transducer 106 is provided. The transmit ultrasonic transducer 104 emits a comparatively narrow ultrasonic beam 107 (less than approximately 10°) that is received by the receive ultrasonic transducer 106, which also has a comparatively narrow acceptance angle (less than approximately 10°)

The transmit and receive transducers 104, 105 are arranged in at an angular offset relative to one another, and as shown in FIG. 1. The overall angular arrangement is required to avoid the creation of standing waves (i.e., through constructive or destructive interference) between the transducers 104, 105 and the absorptive media that is placed between the transducers 104, 105. In addition, the transmit and receive transducers 104, 105 are also tilted to avoid standing waves between transmit ultrasonic transducer 104 and the receive ultrasonic transducer 106. As can be appreciated by one of ordinary skill in the art, such standing waves can adversely impact the detected amplitude of the acoustic waves at the receive transducer 106. In applications that rely on comparatively accurate amplitude measurement and detection, such as absorption measurements, standing waves produce an unacceptable level of measurement uncertainty.

While the known ultrasonic apparatus setup 100 is useful in reducing the occurrence of standing waves between the transmit and receive transducers 104, 106, there are drawbacks to the apparatus 100. For example, the precise location the first and second receptacles 103, 105 adds to the complexity of fabrication of the supports 101, 102. Moreover, because of the comparatively narrow ultrasonic beam 107, alignment tolerances are relatively tight, and add a labor-intensive step to the manufacturing process. Ultimately, the cost of the final product, or the accuracy of the alignment of the transducers 104, 106, or both, can be adversely impacted. Furthermore, the angular offset of the transducers 104, 106 requires an inefficient use of space, and therefore impedes the desire to reduce the overall size of the device 100 for use in certain applications.

What is needed, therefore, is an apparatus that overcomes at least the drawbacks of known transducers discussed above.

SUMMARY

In accordance with a representative embodiment, an apparatus comprises: a first transducer support configured to receive a first transducer in a first opening, wherein a face of the first face of the first transducer is located in a first plane; and a second transducer support configured to receive a second transducer in a second opening. A face of the second transducer is located in a second plane that is substantially parallel to the first plane.

In accordance with another representative embodiment, an ultrasonic device comprises: a first transducer support comprising a first opening; a first ultrasonic transducer disposed in said first opening, the first ultrasonic transducer having a first width substantially equal in magnitude to a first wavelength of transmission or reception of the first ultrasonic transducer, wherein a face of the first face of the first transducer is located in a first plane; a second transducer support comprising a second opening; and a second ultrasonic transducer disposed in the second opening, the second ultrasonic transducer having a second width substantially equal in magnitude to a second wavelength of transmission or reception of the second ultrasonic transducer. A face of the second transducer is located in a second plane.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

As used herein, the terms 'a' or 'an', as used herein are defined as one or more than one.

In addition to their ordinary meanings, the terms 'substantial' or 'substantially' mean to with acceptable limits or degree to one having ordinary skill in the art. For example, 'substantially cancelled' means that one skilled in the art would consider the cancellation to be acceptable.

In addition to their ordinary meanings, the terms 'approximately' mean to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known devices, materials and manufacturing methods may be omitted so as to avoid obscuring the description of the representative embodiments. Nonetheless, such devices, materials and methods that are within the purview of one of ordinary skill in the art may be used in accordance with the representative embodiments.

Figure 2A:
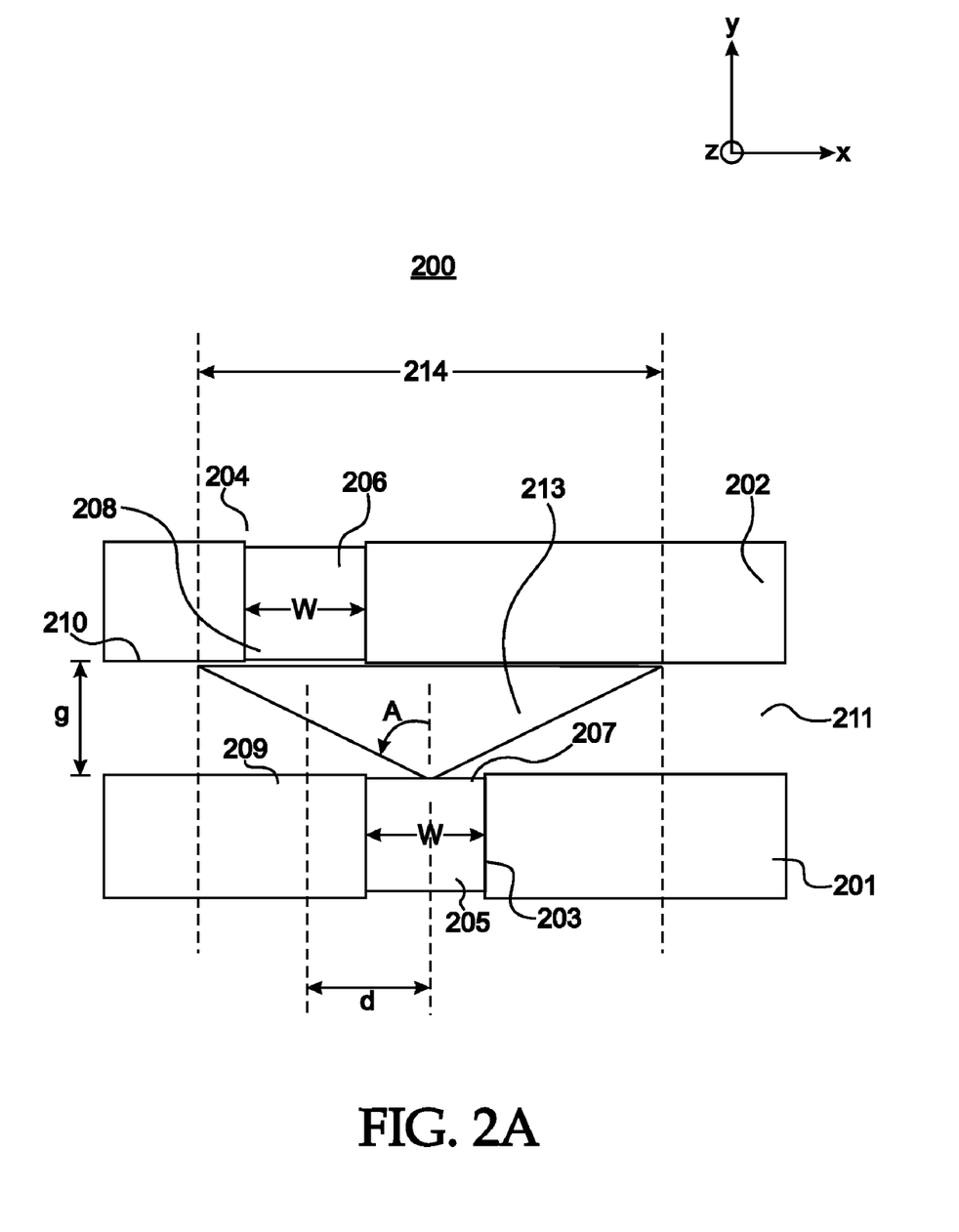
FIG. 2A depicts an apparatus in accordance with a representative embodiment.

FIG. 2A depicts an apparatus 200 in accordance with a representative embodiment. The apparatus 200 comprises a first transducer support 201 and a second transducer support 202. The first transducer support 201 comprises a first opening 203, and the second transducer support 202 comprises a second opening 204. A first transducer 205 is disposed in the first opening 203; and the second transducer 206 is disposed in the second opening 204. As described more fully below, the first and second transducers 205, 206 may be one of a variety of comparatively broad beam (or comparatively wide beam) ultrasonic transducers such as micromachined ultrasonic transducers MUTs.

The first transducer 205 comprises a first face 207 and the second transducer 206 comprises a second face 208. In representative embodiments, the first and second faces 207, 208 have a linear dimension 'w' (i.e., diameter if the face of the transducer is substantially circular) that is comparable to the wavelength of the emitted radiation of the first and second transducers 205, 206. This relative dimensionality ensures broad beam transmission and large acceptance angle of the first and second transducers 205, 206, as described from simple acoustic models such as pistons. The first transducer 205 is seated in first opening 203 so that the first face 207 is substantially flush with a first inner surface 209. The second transducer 206 is seated in second opening 204 so that the second face 208 is substantially flush with a second inner surface 210.

As shown in FIG. 2A, the first inner surface 209 opposes the second inner surface 210; and is separated by a gap 211 from the second inner surface 210. Accordingly, the placement of the first transducer 205 in the first opening 203, and the second transducer in the second opening 204, results in the placement of the first face 207 (in an x-z plane) and the second face 208 (in an x-z plane) in an opposing relationship and separated by gap 211 (shown with dimension 'g' in FIG. 2A). The first face 207 of the first transducer 205 and the second face 208 of the second transducer 206 can be parallel to each other (i.e., located parallel planes). Moreover, the first and second openings 203 and 204 are located in a manner such that the first and second transducers 205, 206 are laterally offset from one another with an offset distance 'd' (shown in FIG. 2A), where 'd' is the distance from the center of second transducer 206 to the center of first transducer 205. It is emphasized that the lateral offset of the first and second transducers 205, 206, and thereby first and second faces 207, 208 is merely illustrative. Lateral offsets less than that shown, and greater than that shown are contemplated. However, to minimize the formation of standing waves between the first and second transducers 205, 206, the offset 'd' should not be less than 'w.' Furthermore, to ensure the reception of sufficient power from the transmitting transducer (e.g., 205) to the receiving transducer (e.g., 206), the lateral offset should not be greater than the tangent of beam angle 'A' times the separation g: $d \leq \tan(A)*g$.

In a representative embodiment, the first transducer 205 functions as the transmitter, and provides a comparatively wide beam ultrasonic signal 213, having a width 214 (where width 214 is equal to $2*\tan(A)*g$) at a plane of incidence, which is the plane of the second face 208 of the second transducer 206. Illustratively, the beam angle 'A' of the first transducer 205 is in the range of approximately 15° to approximately 80°. The second transducer 206 acts as a receiver with a comparatively large acceptance angle. Illustratively, the acceptance angle of the second transducer 206 is in the range of approximately 15° to approximately 80°. The relative location of the first and second transducers 205, 206 in the apparatus 200, the comparatively large width 214 of the ultrasonic signal 213, and the comparatively large acceptance angle of second transducer 206 allows for the reception of sufficient power from the portion of the beam incident on the second face 208 of the second transducer 206 to allow for accurate measurement, such as degree of absorption by an object (e.g., solid, liquid or gas) located in or traversing the gap 211. Moreover, because of the lateral offset of the first and second transducers 205, 206 the forming of standing waves is substantially avoided. For example, because the angle of incidence of the ultrasonic wave is equal to the angle of reflection of the ultrasonic wave, much of the power of the ultrasonic signal 213 reflected from the second transducer 206 and the second inner surface 210 is not reflected back toward the first transducer 205. Beneficially, by laterally offsetting the transducers in the manner of the representative embodiments, the establishment of deleterious standing waves is substantially avoided; yet a sufficient portion of the ultrasonic signal 213 is incident on the second face 208 of the second transducer 206 so that sufficient ultrasonic power is transmitted to the second transducer 206 across the gap 211.

The first and second openings 203, 204 are shown to extend through the thickness of their respective first and second transducer supports 201, 202, for ease of seating, mounting and replacing the first and second transducers 205, 206. This is merely illustrative, and the first and second openings 203, 204 are contemplated to be mounted in cavities (not shown). The various features to the required tolerances of the first and second transducer supports 201, 202 may be fabricated using known machining methods. Moreover, the first and second transducer supports 201, 202 may be fabricated from plastic materials, metals, metal alloys, or ceramic materials, or a combination thereof.

Figure 2B:
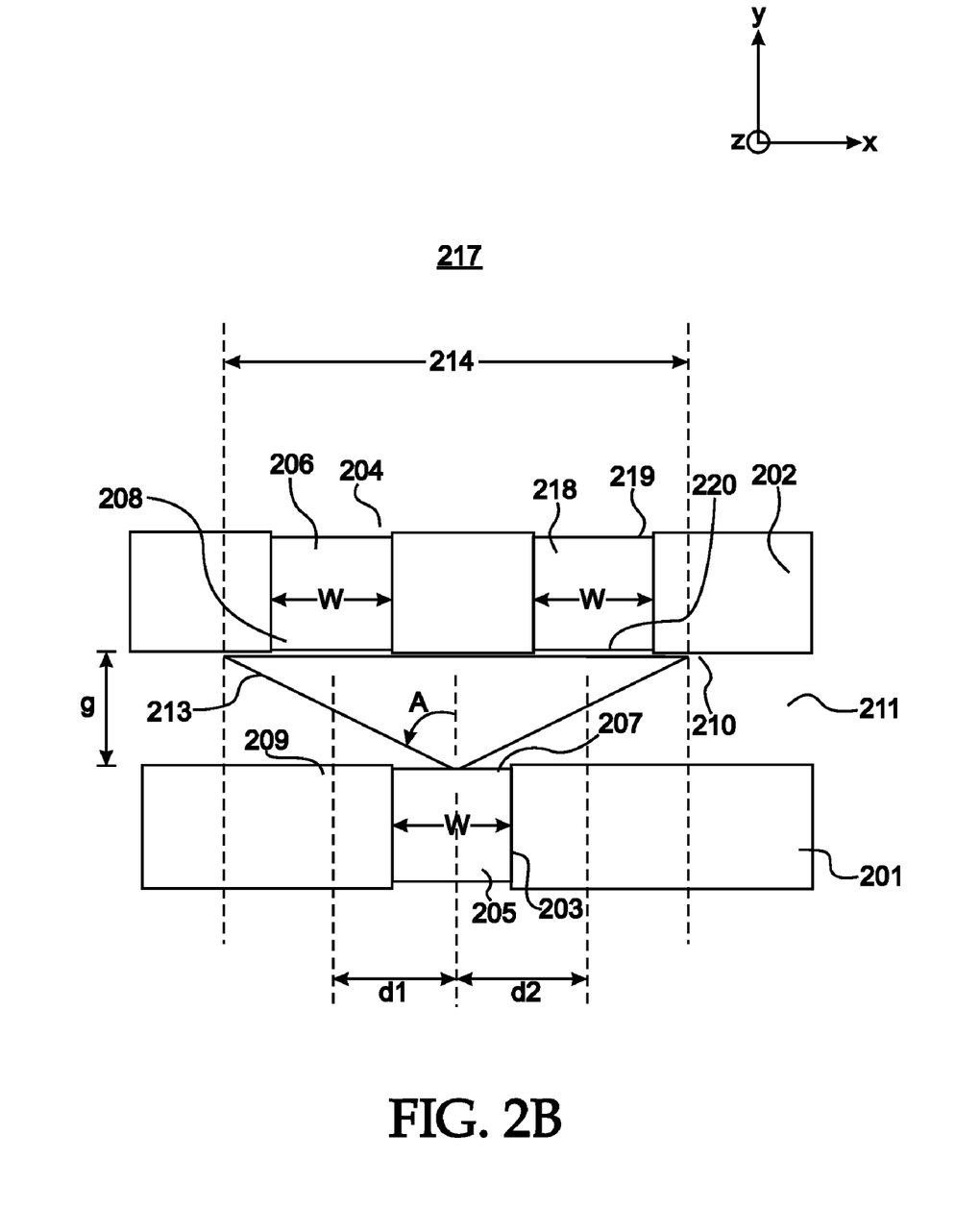
FIG. 2B depicts an apparatus in accordance with a representative embodiment.

FIG. 2B depicts an apparatus 217 in accordance with a representative embodiment. Many of the details of the apparatus 200 described above are common to the description of apparatus 217, and are therefore not repeated to avoid obscuring the description of the representative embodiments. The apparatus 217 comprises a third transducer 218 disposed in a third opening 219 in the second transducer support 202. The third transducer 218 comprises a third face 220 that is illustratively substantially flush with the plane of the second inner surface 210. As shown, a portion of the ultrasonic signal 213 is incident on the third face 220 of the third transducer 218. The third transducer 218 is placed such that the third face 220 is significantly parallel to first face 207. Moreover, second transducer 218 has an offset d2 with respect to first transducer 205 that does not have to be equal to d1.

In the representative embodiment, the first transducer 205 functions as the transmitting transducer, and the second and third transducers 206, 218 function as receiving transducers. The first transducer 205 provides the comparatively wide beam ultrasonic signal 213, with a transmission angle in the range of approximately 15° to approximately 80°. The beam has a width 214 at a plane of incidence (an x-z plane), which is the plane of the second face 208 of the second transducer 206, and the third face 220 of the third transducer 218. The receive first and third transducers 205 and 218 have a comparatively wide acceptance angle; again in the range of approximately 15° to approximately 80°. The relative location of the first, second and third transducers 205, 206 and 218 in the apparatus 217 and the comparatively large width 214 of the ultrasonic signal and the large acceptance angle of the receive transducers allows for the reception of additional acoustic power from the portion of the beam of ultrasonic signal 213 incident on the third face 220 of the third transducer 218. Thus, additional signal reception can be realized in an effort to improve accuracy of a measurement, such as degree of absorption by an object (e.g., solid, liquid, or gas) located in or traversing the gap 211.

Moreover, and like the apparatus 200, because of the lateral offset of the first and second transducers 205, 218 the forming of standing waves is substantially avoided. For example, because the angle of incidence of the ultrasonic wave is equal to the angle of reflection of the ultrasonic wave, much of the power of the ultrasonic signal 213 reflected from the third transducer 218 and the second inner surface 210 is not reflected back toward the first transducer 205. Beneficially, by laterally offsetting the first and second transducers 205, 218 in the manner of the representative embodiments, the establishment of deleterious standing waves between the first transducer 205 and the third transducer 218 is substantially avoided; yet a sufficient portion of the ultrasonic signal 213 is incident on the second face 208 of the second transducer 206, and the third face 220 of the third transducer 218 so that sufficient ultrasonic power is transmitted to the second transducer 206 and the third transducer 218 across the gap 211.

In connection with FIGS. 3A-4C various embodiments of transducers useful in the apparatus 200 are described below. Illustratively, transducers comprises piezoelectric micromachined ultrasonic transducer (pMUT) described in accordance with the present teachings. PMUTs are illustratively based on film bulk acoustic (FBA) transducer technology or hulk acoustic wave (BAW) technology. It is emphasized that pMUTs are merely illustrative, and that other types of transducers, such as capacitive micromachined ultrasonic transducers (cMUTs), are also contemplated. The transducers described below can be configured to transmit comparatively wide beam ultrasonic signals and to receive ultrasonic signals but connection to suitable transmission (driver) circuitry and suitable receive (detection) circuitry (not shown). As such, and depending on their configuration, the transducers may be implemented as first and second transducers 205, 206, 218 of the representative embodiments described above in connection with FIGS. 2A~2B. It is emphasized that the transducers described below are merely illustrative and other transducers configured to provide comparatively wide beam ultrasonic signals are contemplated for use in connection with the embodiments of FIGS. 2A~2B.

Figure 3A:
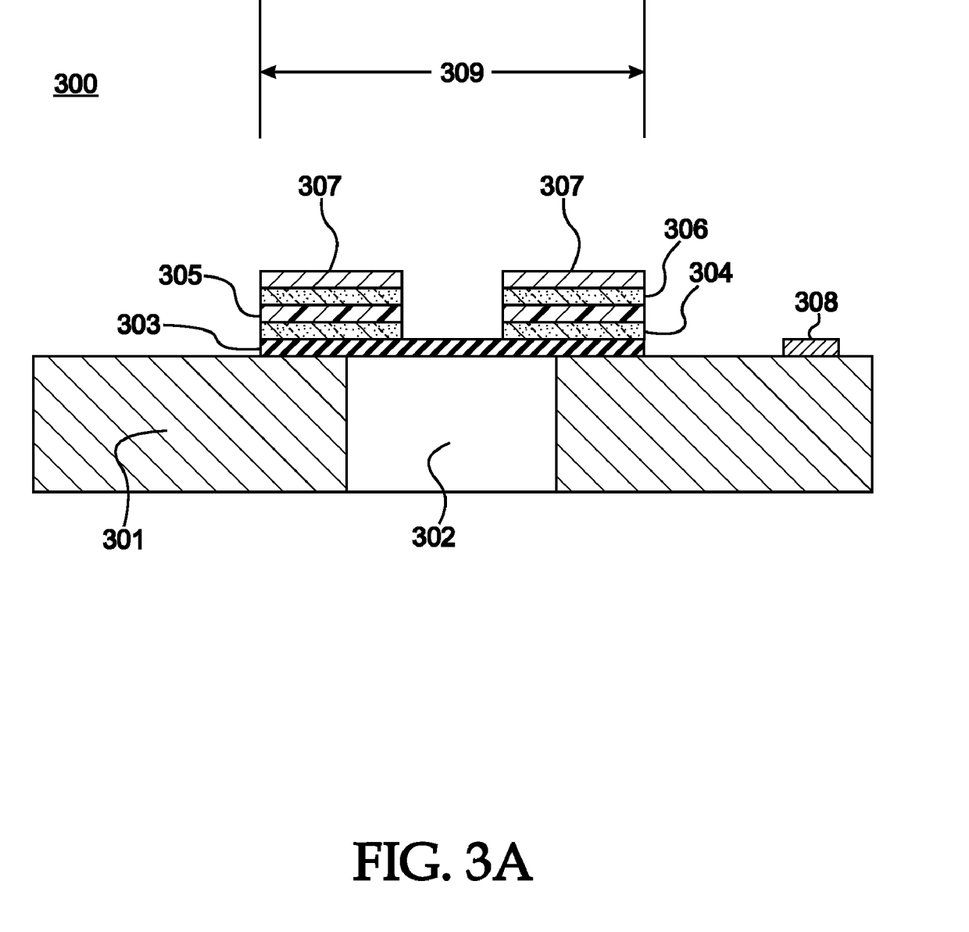
FIG. 3A depicts a cross-sectional view of piezoelectric micromachined ultrasonic transducer (pMUT) in accordance with a representative embodiment.
Figure 3B:
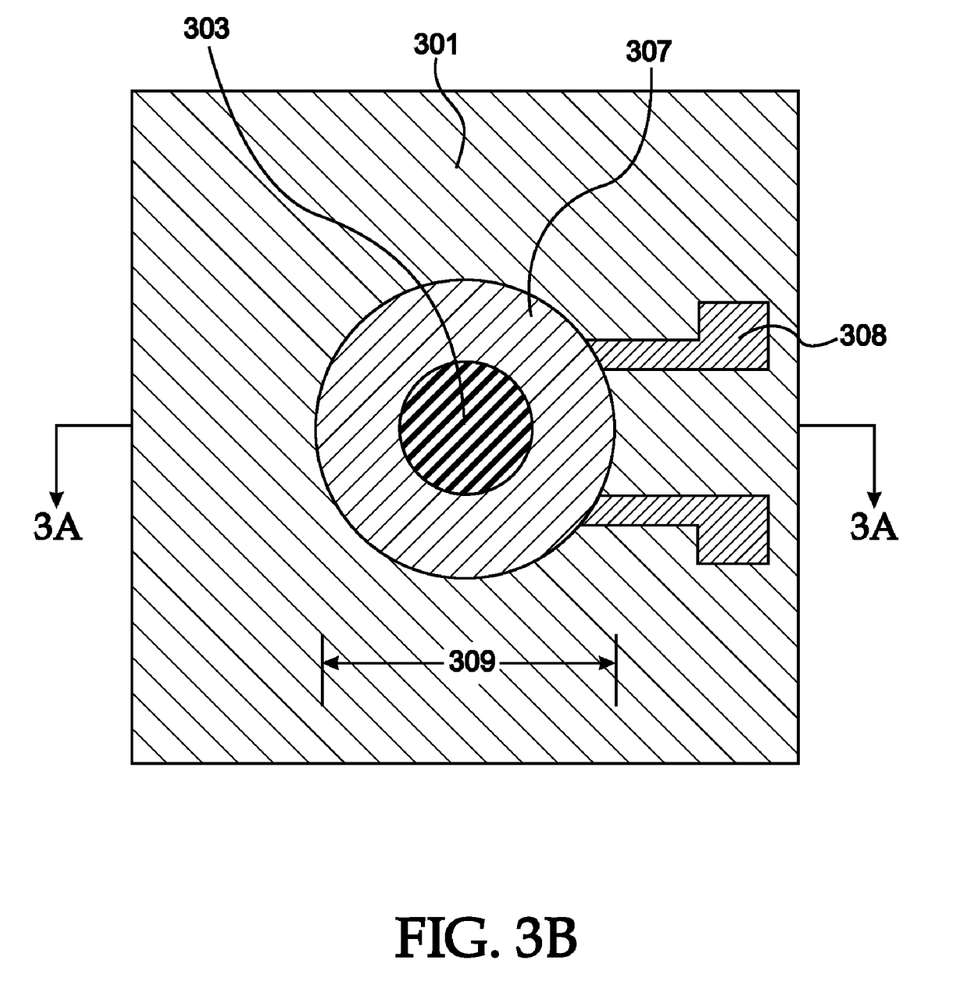
FIG. 3B illustrates a top view of the pMUT depicted in FIG. 3A.

FIG. 3A shows a cross-sectional view of a transducer 300 in accordance with a representative embodiment. FIG. 3B shows a top view of the transducer 300. The cross-section is taken along line 3A-3A. The transducer comprises a substrate 301, which is illustratively silicon (Si) or other suitable material compatible with known semiconductor processing methods. A cavity 302 is provided in the substrate 301. The transducer 300 also comprises a membrane 303, which is formed over the substrate 301 and spans the cavity 302 in the substrate. In a representative embodiment, the membrane may be poly-silicon, Silicon Nitride, Silicon Carbide, Boron Silicate Glass of Phospho-Silicate Glass. It is emphasized that these materials are merely illustrative and that other materials, which are suitable for use as the membrane 303, and which are compatible with selected semiconductor processing methods used to fabricate the transducer 300, are also contemplated.

Because the cavity does not extend through the thickness in the presently described embodiment, the membrane 303 is substantially sealed. It may be necessary to equalize the pressure between both sides of the membrane 303. Illustratively, this can be achieved by providing a hole (not shown) in the membrane 303 or in the substrate 301, or both to equalize the pressure between the cavity on one side of the membrane 303 and the opposing side of the membrane 303 above the device. Alternatively, the cavity 302 may extend through the thickness of the substrate.

The cavity 302 may be formed by known etching methods to include wet etching and drying etching techniques known to one of ordinary skill in the art. For example, the cavity 302 may be provided by a known deep reactive ion etching (DRIE) method, such as the so-called 'Bosch Method' in order to provide the opening with a desired aspect ratio. Notably, the opening may be provided before or after the forming of other components of the transducer described below.

A lower electrode 304 is provided over the membrane 303. In the representative embodiment, the lower electrode 304 is substantially annular. In accordance with a representative embodiment, the lower electrode 304 may comprise a metal such as Molybdenum, Tungsten or Aluminum, or suitable alloys thereof which compatible with semiconductor processes.

A piezoelectric layer 305 is provided over the tower electrode 304 using a known method. In the present embodiment, the piezoelectric layer 305 is also substantially annular, and has approximately the same size and shape as the lower electrode 304. The piezoelectric layer 305 may be a piezoelectric film such as Aluminum Nitride (AlN), Lead-Zirconium Titanate (PZT), Zinc-Oxide (ZnO) or other film compatible with semiconductor processes used in the fabrication of the transducer 300.

An upper electrode 306 is provided over the membrane 303. In the present embodiment, the upper electrode 306 is substantially annular and has approximately the same size and shape as the lower electrode 304, and piezoelectric layer 305. The upper electrode 306 may be a made of the same material as the lower electrode 304.

The transducer 300 optionally comprises a passivation layer 307 to protect the lower electrode 304, the piezoelectric layer 305 and the upper electrode 306 from environmental factors such as humidity. Finally, contacts pads 308 are provided to connect the transducer 300 to transmitter circuitry (not shown), or receiver circuitry (not shown), or both. The contact pads 308 are connected to the top and bottom electrodes and are made following standard semiconductor manufacturing processes.

The transducer 300 has an active area diameter 309. According to a representative embodiment, the diameter 309 is selected to be on the order of magnitude of the wavelength of the ultrasonic signal transmitter or received by the transducer. For example, the diameter 309 is selected to be on the order of magnitude of the ultrasonic signal 213. By selecting the diameter 309 to be of the magnitude of the wavelength of the ultrasonic signal, a comparatively broad or wide beam width is attained. Accordingly, the arrangement of the first and second transducers 205, 206, 218 in the representative embodiments described in connection with FIGS. 2A~2B can be realized using the comparatively wide beam ultrasonic signal 213, with only a portion of the signal from first transducer 205 being incident on the second and third transducers 206, 218.

Figure 4A:
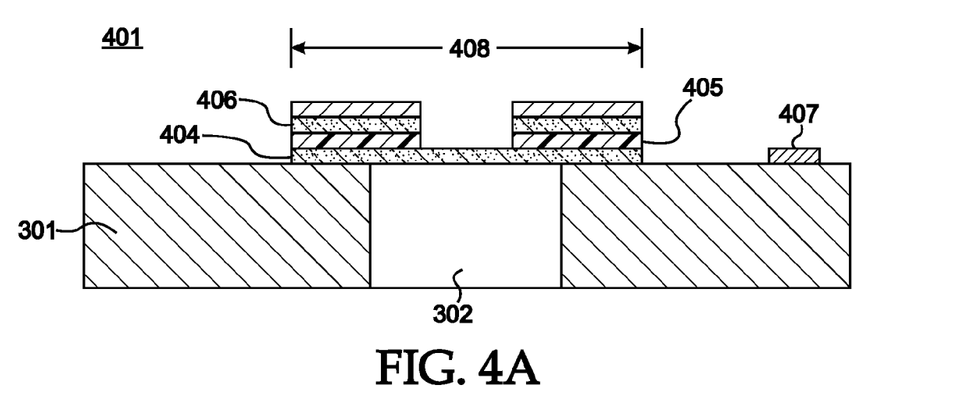
FIGS. 4A-4C depict cross-sectional views of pMUTs in accordance with representative embodiments.
Figure 4B:
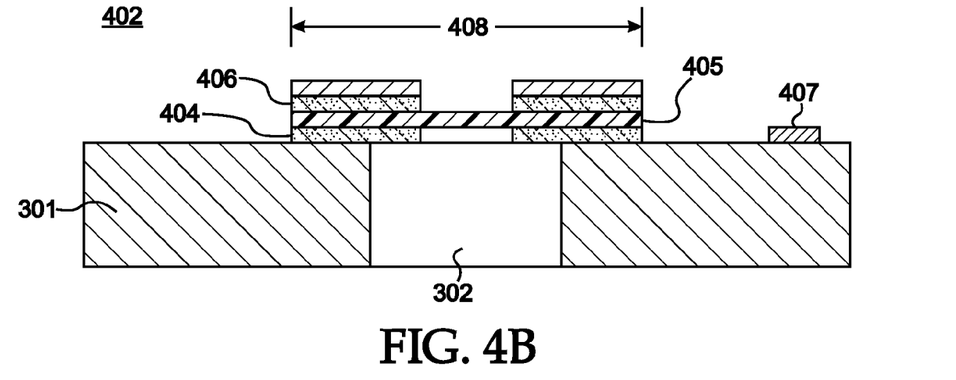
Figure 4C:
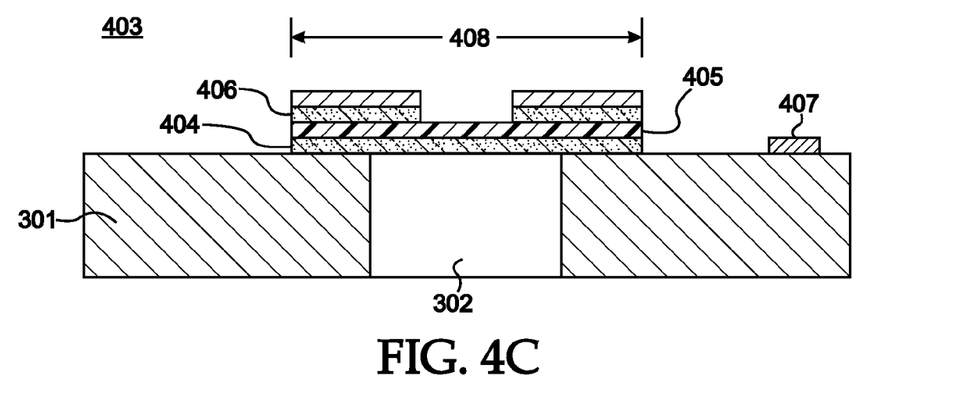

FIGS. 4A-4C show cross-sectional views of pMUTs 401, 402 and 403, respectively. The pMuts 401~403 comprise many features common to the transducer 300 described above. Many common details of the pMUTs are not repeated to avoid obscuring the description of the present embodiments.

pMUT 401 comprises substrate 301 with cavity 302. A lower electrode 404 is provided over and spans the cavity 302. In the representative embodiment, the lower electrode 404 is substantially circular and has a diameter 408. In accordance with a representative embodiment, the lower electrode 404 may comprise a metal such as Molybdenum, Tungsten or Aluminum, or suitable alloys thereof, which compatible with semiconductor processes. A piezoelectric layer 405 is provided over the lower electrode 404 using a known method. In the present embodiment, the piezoelectric layer 405 is substantially annular, and has approximately the same diameter as the lower electrode 404. The piezoelectric layer 405 may be a piezoelectric film such as Aluminum Nitride (AlN), Lead-Zirconium Titanate (PZT), Zinc-Oxide (ZnO) or other film compatible with semiconductor processes used in the fabrication of the pMUT 401. An upper electrode 406 is provided over the piezoelectric layer 405. In the present embodiment, the upper electrode 406 is substantially annular and has approximately the same size and shape as piezoelectric layer 405. The upper electrode 406 may be a made of the same material as the lower electrode 404.

pMUT 402 comprises substrate 301 with cavity 302. In the representative embodiment, the lower electrode 404 is substantially annular and has diameter 408. In accordance with a representative embodiment, the lower electrode 404 may comprise a metal such as Molybdenum, Tungsten or Aluminum, or suitable alloys thereof, which compatible with semiconductor processes. A piezoelectric layer 405 is provided over the lower electrode 404 using a known method. In the present embodiment, the piezoelectric layer 405 is substantially circular, and has approximately the same diameter as the lower electrode 404. As shown, the piezoelectric layer 405 spans the cavity 302. The piezoelectric layer 405 may be a piezoelectric film such as Aluminum Nitride (AlN), Lead-Zirconium Titanate (PZT), Zinc-Oxide (ZnO) or other film compatible with semiconductor processes used in the fabrication of the pMUT 401. An upper electrode 406 is provided over the piezoelectric layer 405. In the present embodiment, the upper electrode 406 is substantially annular and has approximately the same size and shape as lower electrode 404. The upper electrode 406 may be a made of the same material as the lower electrode 404.

pMUT 403 comprises substrate 301 with cavity 302. A lower electrode 404 is provided over and spans the cavity 302. In the representative embodiment, the lower electrode 404 is substantially circular and has a diameter 408. In accordance with a representative embodiment, the lower electrode 404 may comprise a metal such as Molybdenum, Tungsten or Aluminum, or suitable alloys thereof, which compatible with semiconductor processes. A piezoelectric layer 405 is provided over the lower electrode 404 using a known method. In the present embodiment, the piezoelectric layer 405 is substantially circular, and has approximately the same diameter as the lower electrode 404. The piezoelectric layer 405 may be a piezoelectric film such as Aluminum Nitride (AlN), Lead-Zirconium Titanate (PZT), Zinc-Oxide (ZnO) or other film compatible with semiconductor processes used in the fabrication of the pMUT 401. An upper electrode 406 is provided over the piezoelectric layer 404. In the present embodiment, the upper electrode 406 is substantially annular and has approximately the same size and shape as piezoelectric layer 405. The upper electrode 406 may be a made of the same material as the lower electrode 404.

In view of this disclosure it is noted that the MEMs devices, transducers and apparatuses can be implemented in a variety of materials, variant structures, configurations and topologies. Moreover, applications other than small feature size transducers may benefit from the present teachings. Further, the various materials, structures and parameters are included by way of example only and not in any limiting sense. In view of this disclosure, those skilled in the art can implement the present teachings in determining their own applications and needed materials and equipment to implement these applications, while remaining within the scope of the appended claims.

The invention claimed is:

1. An apparatus, comprising:
a first transducer support configured to receive a first transducer in a first opening, wherein a face of the first face of the first transducer is located in a first plane;
a second transducer support configured to receive a second transducer in a second opening, wherein a face of the second transducer is located in a second plane that is substantially parallel to the first plane, wherein the face of the first transducer is substantially coplanar with the first opening, and the face of the second transducer is substantially coplanar with the second opening.

2. An apparatus as claimed in claim 1, wherein the first opening is linearly offset from the second opening.

3. An apparatus as claimed in claim 2, wherein the first transducer is configured to transmit an ultrasonic signal and the second transducer is configured to receive a portion of the ultrasonic signal.

4. An apparatus as claimed in claim 1, further comprising a third opening in the second transducer support, the third opening being configured to receive a third ultrasonic transducer.

5. An apparatus as claimed in claim 4, wherein a face of the third transducer is substantially coplanar with the third opening and the second opening.

6. An apparatus as claimed in claim 5, wherein the first opening is linearly offset from the second opening.

7. An apparatus as claimed in claim 4, wherein the first transducer is configured to transmit an ultrasonic signal, and the second transducer and the third transducer are each configured to receive respective portions of the ultrasonic signal.

8. An apparatus as claimed in claim 1, wherein the first and second transducers each comprise a piezoelectric transducer.

9. An apparatus as claimed in claim 8, wherein the ultrasonic transducers comprise piezoelectric micromachined transducers (pMUTs).

10. An apparatus as claimed in claim 3, wherein the first transducer is configured to transmit the ultrasonic beam having a beam angle in the range of approximately 15° to approximately 80°.

11. An apparatus as claimed in claim 3, wherein the second transducer is configured to receive the ultrasonic signal within an acceptance angle in the range of approximately 15° to approximately 80°.

12. An ultrasonic device, comprising:
a first transducer support comprising a first opening;
a first ultrasonic transducer disposed in said first opening, the first ultrasonic transducer having a first width substantially equal in magnitude to a first wavelength of transmission or reception of the first ultrasonic transducer, wherein a face of the first face of the first transducer is located in a first plane;
a second transducer support comprising a second opening; and
a second ultrasonic transducer disposed in the second opening, the second ultrasonic transducer having a second width substantially equal in magnitude to a second wavelength of transmission or reception of the second ultrasonic transducer, wherein a face of the second transducer is located in a second plane.

13. An ultrasonic device as claimed in claim 12, wherein the face of the first transducer is substantially coplanar with the first opening, and the face of the second transducer is substantially coplanar with the second opening.

14. An ultrasonic device as claimed in claim 12, wherein the first opening is linearly offset from the second opening.

15. An ultrasonic device as claimed in claim 12, further comprising a third opening in the second transducer support, the third opening being configured to receive a third ultrasonic transducer.

16. An ultrasonic device as claimed in claim 15, wherein a face of the third transducer is substantially coplanar with the third opening and the second opening.

17. An ultrasonic device as claimed in claim 15, the third ultrasonic transducer comprises a third width substantially equal in magnitude to a third wavelength of transmission or reception of the third ultrasonic transducer, wherein a face of the third transducer is located in a third plane.

18. An ultrasonic device as claimed in claim 12, wherein the first wavelength and the second wavelength are substantially equal.

19. An ultrasonic device as claimed in claim 17, wherein the first wavelength, the second wavelength and the third wavelength are substantially equal.

* * * * *